(12) United States Patent
McGimpsey et al.

(10) Patent No.: US 8,357,662 B2
(45) Date of Patent: Jan. 22, 2013

(54) SURFACE-BASED AMMONIUM ION SENSOR AND METHODS OF MAKING THEREOF

(75) Inventors: W. Grant McGimpsey, Worcester, MA (US); Nantanit Wanichacheva, Worcester, MA (US); Christopher R. Lambert, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 461 days.

(21) Appl. No.: 12/440,328

(22) PCT Filed: Sep. 10, 2007

(86) PCT No.: PCT/US2007/078005
§ 371 (c)(1),
(2), (4) Date: Aug. 2, 2010

(87) PCT Pub. No.: WO2008/031091
PCT Pub. Date: Mar. 13, 2008

(65) Prior Publication Data
US 2010/0290951 A1    Nov. 18, 2010

Related U.S. Application Data

(60) Provisional application No. 60/843,351, filed on Sep. 8, 2006.

(51) Int. Cl.
*A61K 38/12* (2006.01)
*C07K 7/50* (2006.01)
*C07K 7/54* (2006.01)
(52) U.S. Cl. .................. 514/21.1; 530/318; 540/454
(58) Field of Classification Search .................. None
See application file for complete search history.

(56) References Cited

U.S. PATENT DOCUMENTS

| 6,746,595 B2 | 6/2004 | Benco et al. |
| 2004/0256227 A1 | 12/2004 | Shin et al. |

OTHER PUBLICATIONS

International Search Report and Written Opinion of the International Searching Authority, dated Aug. 20, 2008 for Corresponding International Patent Application No. PCT/US2007/078005.
Benco, et al., Anal. Chem. Jan. 1, 2003, vol. 75, pp. 152-156, see especially Scheme 1, p. 154.
Wanichacheva, et al., Anal. Chem. Oct. 15, 2006, vol. 78, pp. 7132-7137, see especially Figure 1.

*Primary Examiner* — Noble Jarrell
(74) *Attorney, Agent, or Firm* — Burns & Levinson LLP; Jacob N. Erlich; Janine M. Susan

(57) ABSTRACT

A compound sensitive to and selective for ammonium ions over other ions. A sensor fabricated from a self assembled monolayer of said compound on gold, exhibiting sensitivity and selectivity for ammonium ions over other ions in aqueous solutions, including blood. A method of preparation of said compound and said sensor.

17 Claims, 8 Drawing Sheets

SURFACE-BASED AMMONIUM ION SENSOR AND METHODS OF MAKING THEREOF

CROSS-REFERENCE TO RELATED APPLICATIONS

This application is a U.S. national stage application under 35 U.S.C. 371 of International Application No. PCT/US/78005 filed Sep. 10, 2007 and entitled SURFACE-BASED AMMONIUM ION SENSOR: AN ELECTRODE DERIVATIZED WITH A SELF-ASSEMBLED MONOLAYER, which in turn claims priority to U.S. Provisional Patent Application No. 60/843,351 filed Sep. 8, 2006.

CROSS REFERENCE TO RELATED APPLICATIONS

The present application is being filed under 35 U.S.C. §371 of International Application No. PCT/US2007/078005, filed on Sep. 10, 2007, which claims priority to U.S. Provisional Application Ser. No. 60/843,351, entitled A SURFACE-BASED AMMONIUM ION SENSOR: AN ELECTRODE DERIVATIZED WITH A SELF-ASSEMBLED MONOLAYER, filed on Sep. 8, 2006.

BACKGROUND OF THE INVENTION

Metabolite levels such as the amount of urea and creatinine in blood are important disease indicators. Urea and creatinine levels are measured indirectly using enzyme-catalyzed hydrolysis to produce ammonium ions. Much work has focused on fabricating sensors for selective ammonium ion detection. In clinical use, the measurement of ammonium ion concentrations is achieved by carrier-based ion selective electrodes (ISEs) containing an ionophore, a ligand which has high selectivity and sensitivity to specific ions. The natural antibiotic nonactin is the most widely studied compound used as an ammonium ionophore. However, nonactin-based ammonium ISEs have a limit in their utility due to the poor selectivity of ammonium over potassium ions (log $K_{NH_4^+,K^+}$~−0.9).

Modification of gold surfaces with self-assembled monolayers (SAMs) of organic compounds has received considerable interest due to the potential application of such as microfluidic sensors. The introduction of a selective ionophore in the adsorbates allows the development of rapidly responding chemical sensors. The use of SAMs in sensor technology has typically used electrochemical techniques to transduce the binding of the analyte. Cyclic voltammetry (CV) and impedance spectroscopy (IS) techniques allow the detection of metal cation complexation by the monolayer by measuring changes in conductivity or capacitance. There are reports in the literature of the preparation of SAMs of alkanethiols bearing crown-ethers that can complex non-electrochemically active ions such as $Na^+$ and $K^+$, or metallosalophenes that complex transition metal ions (e.g. $Ni^{2+}$, $Cu^{2+}$ and $Co^{2+}$), whereby the binding processes were studied utilizing CV and impedance techniques. Also there are reports of the studies of ion recognition properties of other molecules on gold, such as helical peptides linked to a crown ether, crown ethers bonded to tetrathiafulvalene disulfides, and alkanethiols modified with nitrilotriacetic acid.

In our previous work an ammonium ionophore based on a cyclic depsi-peptide structure was incorporated into a planar ion-selective electrode (ISE) sensor format, which provides selectivity for $NH_4^+$ against the interfering ions, $Na^+$, and $K^+$, log $K_{NH_4^+,Na^+}$~−2.1 and log $K_{NH_4^+,K^+}$~−0.6. However the electrode require substantial amount of ionophore for fabrication and exhibits long equilibration times, which limits its practical applications.

SUMMARY OF THE INVENTION

The present invention relates to a $NH_4^+$ sensor fabricated from a self assembled monolayer on gold. This sensor is characterized by small size, requires minimum amounts of ionophore material for fabrication and exhibits extremely fast equilibration times. The sensor can be used in aqueous environments. Accordingly, the ionophore moiety was synthesize such that it can attach to the gold surface in order to monitor a transduction mechanism in aqueous media. In one embodiment of this invention monolayers of hexadecanethiol coupled to a cyclic depsipetide molecule with the ability to selectively complex $NH_4^+$ ions were fabricated. The ability of these monolayers to function as sensors was shown by impedance spectroscopy. Impedance experiments in the absence of a redox probe (i.e. only supporting electrolyte) provided reproducible data that shows a change in monolayer capacitance upon ion complexation. The compound showed selectivity for complexation of $NH_4^+$ ions over other ions, with log $K_{NH_4^+,Na^+}$~−1.23 and log $K_{NH_4^+,K^+}$~−1.17. This selectivity differs from the selectively of the same compound in an ISE membrane. This selectivity over potassium ions is superior to that obtained for an ionophore of this compound in an ISE membrane (log $K_{NH_4^+,K^+}$~−0.6), although it is somewhat less selectivity for sodium ions (log $K_{NH_4^+,Na^+}$~−2.1.) This study shows that selective ion complexation can be demonstrated on surfaces using an impedance measurement technique.

For a better understanding of the present invention, together with other and further objects thereof, reference is made to the accompanying drawings and detailed description. The scope of the present invention is pointed out in the appended claims.

DETAILED DESCRIPTION OF THE PREFERRED EMBODIMENTS

The present invention is now described more fully hereinafter with reference to the accompanying drawings, in which the illustrative embodiments of the present invention are shown.

Figure 1:
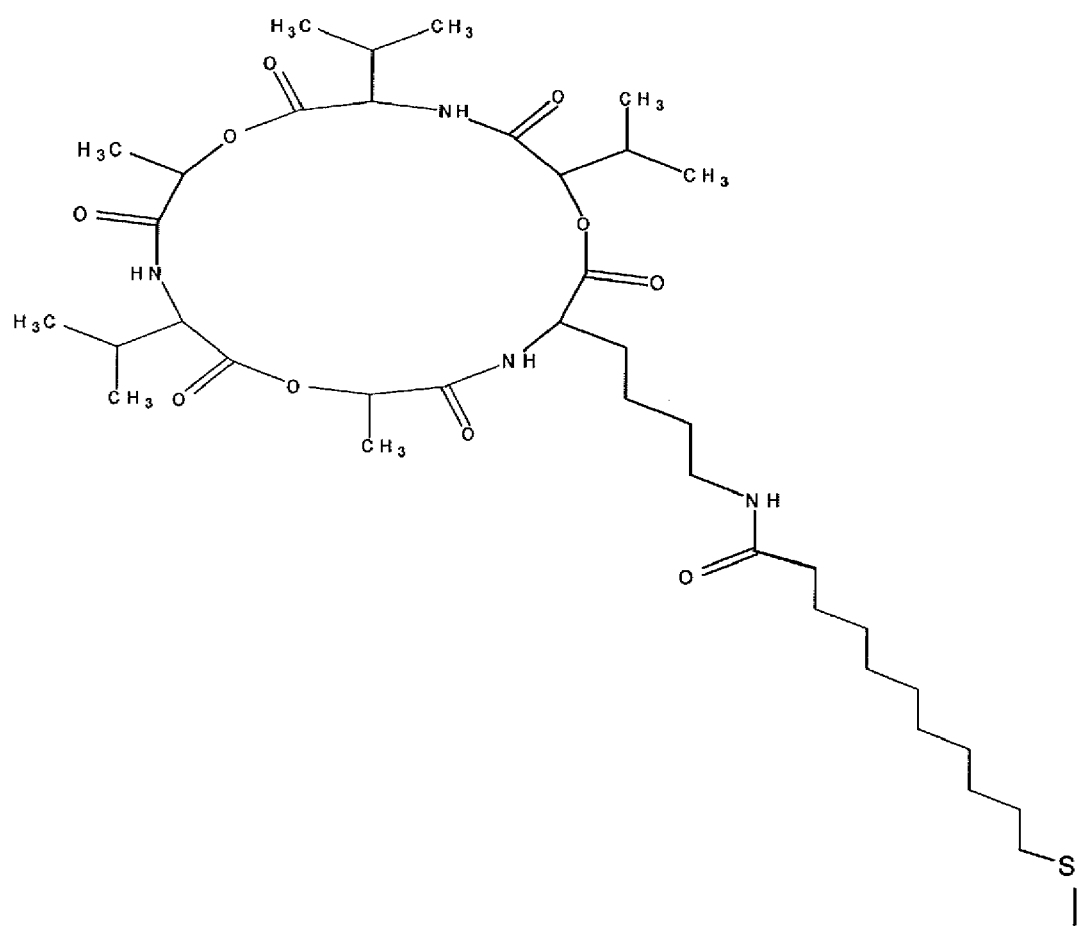
FIG. 1 is a pictorial diagram of an illustrative structure of the $NH_4^+$ sensor on gold surface.

The SAM comprises a single molecular layer of a cyclic depsi-peptide structure shown in FIG. 1. The compound shown in FIG. 1 is a 11-mercapto-N-(4-(9,15,18-triisopropyl-6,12-dimethyl-2,5,8,11,14,17-hexaoxo-1,7,13-trioxa-4,10,16-triazacyclooctadecan-3-yl)butyl) undecanamide, comprising an alkanethiol moiety and a cyclic depsi-peptide moiety. Alkanethiol moiety was used to form a relatively well ordered self-assembled monolayer on gold, with the cyclic depsi-peptide moiety exposed on the surface. This compound was designed following a similar approach that was used for our previously reported ionophores and fluoroionophores. See, Benco, J. S., Nienaber, H. A., McGimpsey, W. G. *Anal. Chem.*, 75, p 152-156 (2003); Benco, J. S., Nienaber, H. A., Dennen, K., McGimpsey, W. G. *J. Photochem. Photobiol., A.*, 152, p 33-40 (2002); Benco, J. S., Nienaber, H. A., Grant McGimpsey, W. Sens. *Actuators, B., B*85, p 126-130 (2002); Benco, J. S.; Nienaber, H. A.; McGimpsey, W. G. J. Photochem. Photobiol., A., 162, p 289-296 (2004); and Wanichecheva, N., Benco, J. S., Lambert, C. R., McGimpsey, W. G. *Photochem. Photobiol*, 82, p 268-273 (2006), the entire teachings of which are incorporated herein by reference. Molecular modeling of the cyclic structure showed that it provides a rigid framework and size fit for an ammonium ion. The ammonium ion binding ability of the surface-bound sensor was monitored by cyclic voltammetry and impedance spectroscopy. Formation of a monolayer on gold was monitored by contact angle, ellipsometry and FT-IR.

Figure 3:
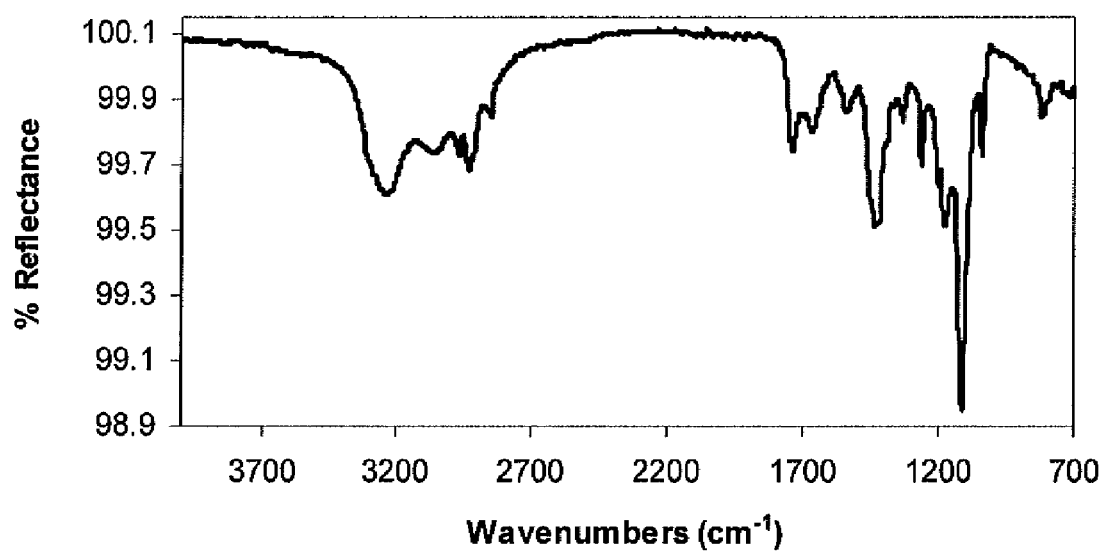
FIG. 3 is a grazing angle FT-IR spectrum of compound I on gold.

Contact angle showed the formation of a slightly hydrophobic layer (46±2°) compared to bare gold (13±2°), and ellipsometry demonstrates the formation of a single layer on the surface (layer thickness: 2.8±0.3 nm). The best evidence of deposition of compound I on gold comes from grazing-incidence infrared spectroscopy (see FIG. 3.) The grazing angle FT-IR spectrum of I on gold shows an absorption peak at 1741 and 1673 $cm^{-1}$ corresponding to the carbonyl group of the ester bonds and amide bonds, respectively. An absorption peak at 1435 $cm^{-1}$ shows the C—N bonds. An absorption peak at 1114 $cm^{-1}$ shows the C—O bonds. Other significant bands in the IR spectra are the methylene stretching vibrations at 2969 and 2933 $cm^{-1}$. The broad band at 3234 $cm^{-1}$ shows the hydrogen bonding.

Figure 4:
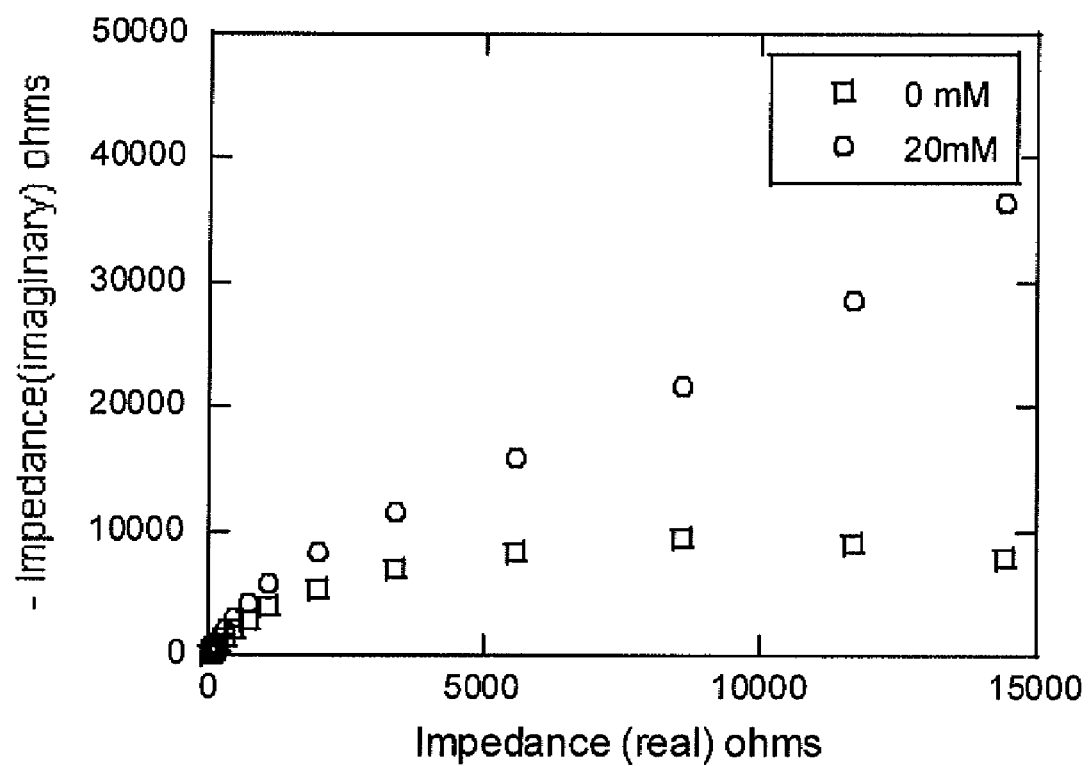
FIG. 4 is a graph of Nyquist plots obtained at −0.5 V vs Ag/AgCl with a supporting electrolyte solution of (1) 0 mM $NH_4Cl$ and 0.1 M tetraethyl ammonium bromide and (2) 20 mM $NH_4Cl$ and 0.08 M tetraethyl ammonium bromide, wherein the inset illustrates the equivalent circuit used to fit the spectra in this study, containing an electrolyte resistance (REL), a monolayer capacitance (CML), a charge-transfer resistance (RCT), and a diffusion element (W)
Figure 5:
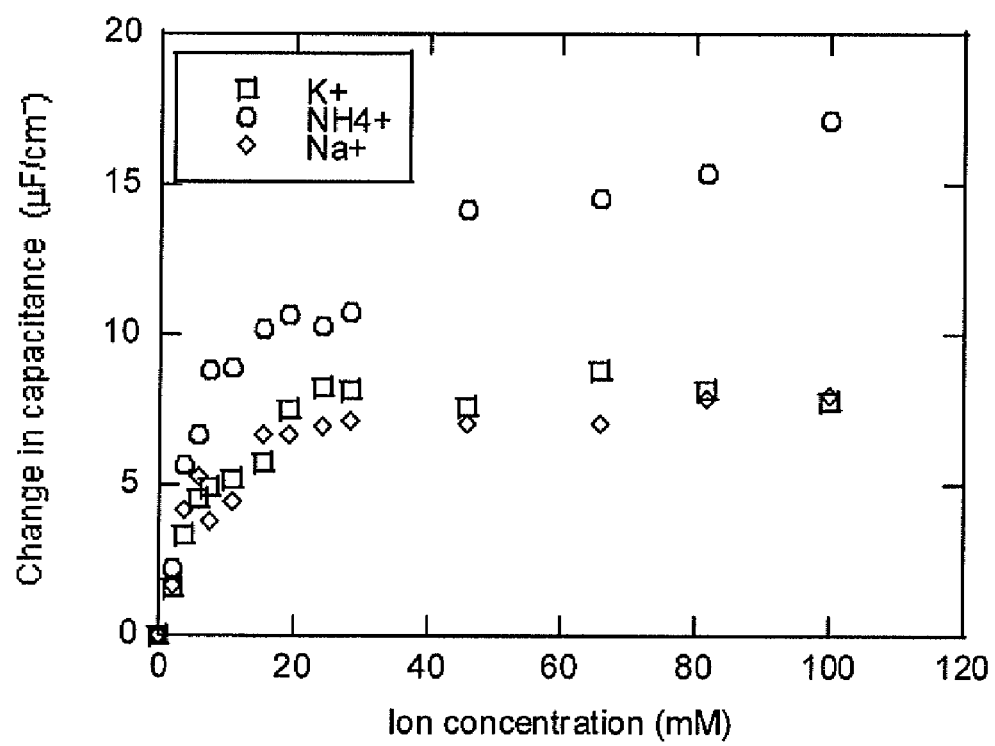
FIG. 5 is a graph of the capacitance of compound I on gold as a function of ion concentration for different ions.

The analysis of the SAM based sensor was carried out using impedance techniques to show the ability of the SAM to bind $NH_4^+$ ions selectively. Experiments were conducted in the presence of a background electrolyte solution of 0.1 M tetraethylammonium chloride at a constant potential of −0.5 V vs a Ag/AgCl reference electrode at different concentrations of $NH_4^+$, $K^+$, $Na^+$ or $Li^+$. The experimental Nyquist plots can then be fit to a model circuit, in this case a Randles equivalent circuit, using non-linear least squares fitting. A Randles circuit consists of a solution resistance in series with the parallel capacitance and resistance of the monolayer. A Warburg element is due to the diffusion limitation at low frequencies. The inset shown in FIG. 4 is the equivalent circuit used to fit the spectra in this study. The capacitance of the monolayer-covered electrode, $C_{ML}$, is proportional to the dielectric constant of the monolayer as shown in the following expression:

$$C_{ML} = \epsilon_0 \epsilon_r A/d$$

where $\epsilon_0$ is the permittivity of vacuum, $\epsilon_r$ is the dielectric constant of the monolayer, A is the surface area and d is the average layer thickness. The capacitance of the monolayer will change in relation to the degree of ion binding because of the increase in the dielectric constant of the film as more metal ions are complexed. Nyquist plots obtained at two different concentrations of $NH_4^+$ ions are shown in FIG. 4. Fitting this data to the previously described equivalent circuit gives capacitance values for the monolayer that are related to metal ion concentration. A plot of capacitance changes vs ion concentration is shown in FIG. 5. The capacitance results show that the SAMs have a lower affinity for $Na^+$ and $K^+$. The complexation of $NH_4^+$ and ionophore I (see FIG. 6) on gold surface was studied to provide evidence that the supporting electrolyte (tetrabutyl ammonium bromide or tetraethyl ammonium chloride) does not significantly interfere in the impedance measurements. The molecular modeling of ionophore I in water using forcefields AMBER94 and MMFF94 showed unstable complexes of ionophore I to tetraethyl ammonium ion. The results show that the capacitance increases as a function of ion concentration until it reaches a plateau, beyond which it is constant up to the maximum concentration tested (0.1 M). FIG. 5 demonstrates that SAMs of this sensor provide selectivity for ammonium ions over potassium and sodium ions with log $K_{NH4^+,Na^+} \sim −1.23$ and log $K_{NH4^+,K^+} \sim −1.17$. Selectivity was calculated by a method used in ion selective electrode applications (see, Bakker, E., Buehlmann, P., Pretsch, E., *Chem. Rev.*, 97, p 3083-3132 (1997), the entire teaching of which is incorporated herein by reference.) Selectivity is represented as a logarithmic value and is calculated using the following equation:

$$\log K_{i,j} = \log([i]/[j])$$

Here, [j] is the concentration of the interfering ion in the plateau region of the plot, where the concentration of the interfering ion provides the maximum capacitance response. The concentration of the primary ion, [i], is the concentration that gives the same response as the maximum capacitance produce by the interfering ion, representing a minimum unambiguous detection limit for the primary ion.

Figure 6:
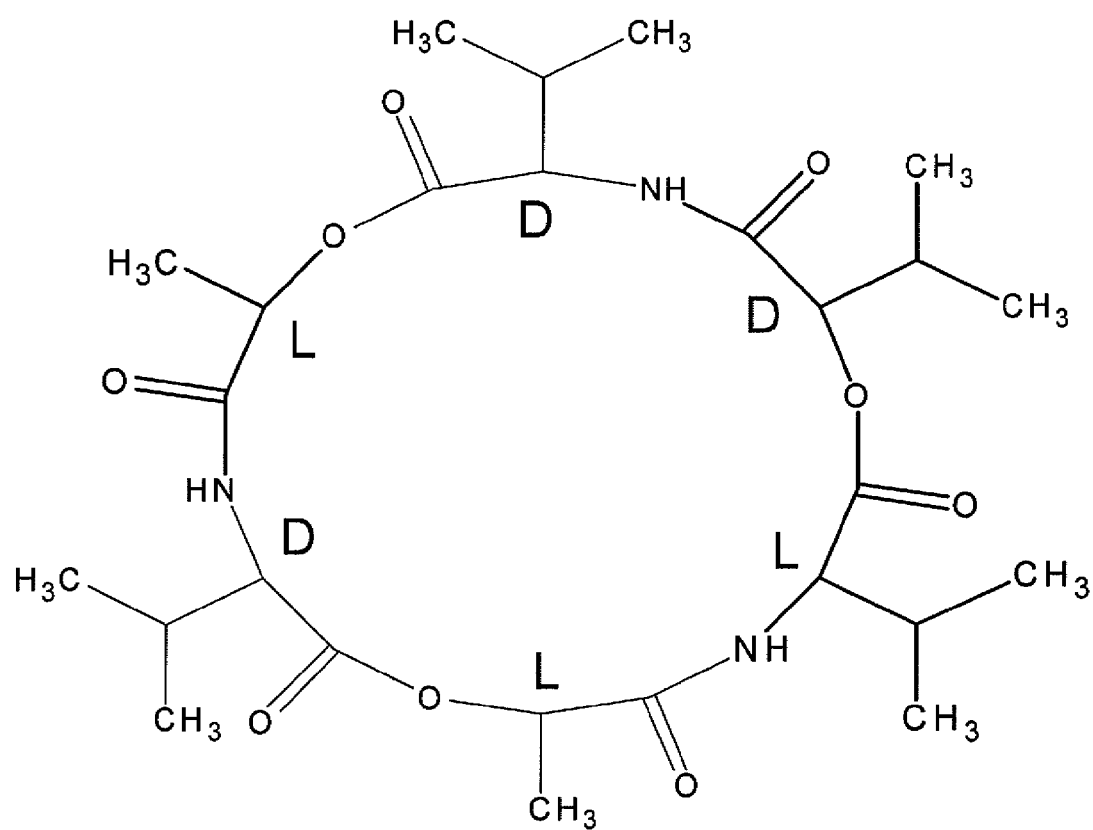
FIG. 6 is a pictorial diagram of the structure of the ionophore of compound I.

The ionophore of compound I has also been used as an ionophore for ion selective electrode format (see FIG. 6.) This ionophore in polyvinylchloride (PVC) membrane provides selectivity for ammonium ions over potassium and sodium ions with log $K_{NH4^+,Na^+} \sim −2.1$ and log $K_{NH4^+,K^+} \sim −0.6$. It is noteworthy that this ionophore appears to exhibit different selectivity in the different formats which has implications for the fabrication of a SAM based on ion selective electrode.

EXAMPLES

All reagents and solvents for synthesis were purchased from Aldrich Chemical (Milwaukee, Wis.), unless otherwise noted. D-Hydroxyisovaleric acid was purchased from Fluka Chemical Corporation (Milwaukee, Wis.). L-Lactic acid was purchased from Alfa Aesar. Amino acids and coupling reagents, Boc-D-Val-OH, Boc-Lys(Fmoc)-OH, benzotriazole-1-yl-oxy-tris-pyrrolidino-phosphonium hexafluorophosphate (PyBOP), and 1-hydroxybenzo-triazole hydrate (HOBT), were purchased from Calbiochem-Novabiochem Corp. (San Diego, Calif.). Electrolyte solutions were freshly prepared using high-purity Millipore deionized water (18 MΩ.cm).

NMR spectra were obtained in an Avance Bruker spectrometer at 400 MHz for proton and 100 MHz for $^{13}C$ NMR spectra were obtained in $CDCl_3$ or MeOD solutions. Mass spectra were measured by SynPep Corporation (Dublin, Calif.) or Water Micromass Model ZMD, Mass Spectrometer. Ionization was performed using electrospray, with an aqueous solution of acetonitrile or methanol as the carrier solvent, and nitrogen as a curtain gas. Melting point data was obtained using a MeI-Temp capillary melting point apparatus and were not corrected.

Example 1

Synthesis of 11-mercapto-N-(4-(9,15,18-triisopropyl-6,12-dimethyl-2,5,8,11,14,17-hexaoxo-1,7,13-trioxa-4,10,16-triazacyclooctadecan-3-yl)butyl)undecanamide (Compound I)

Figure 2A:
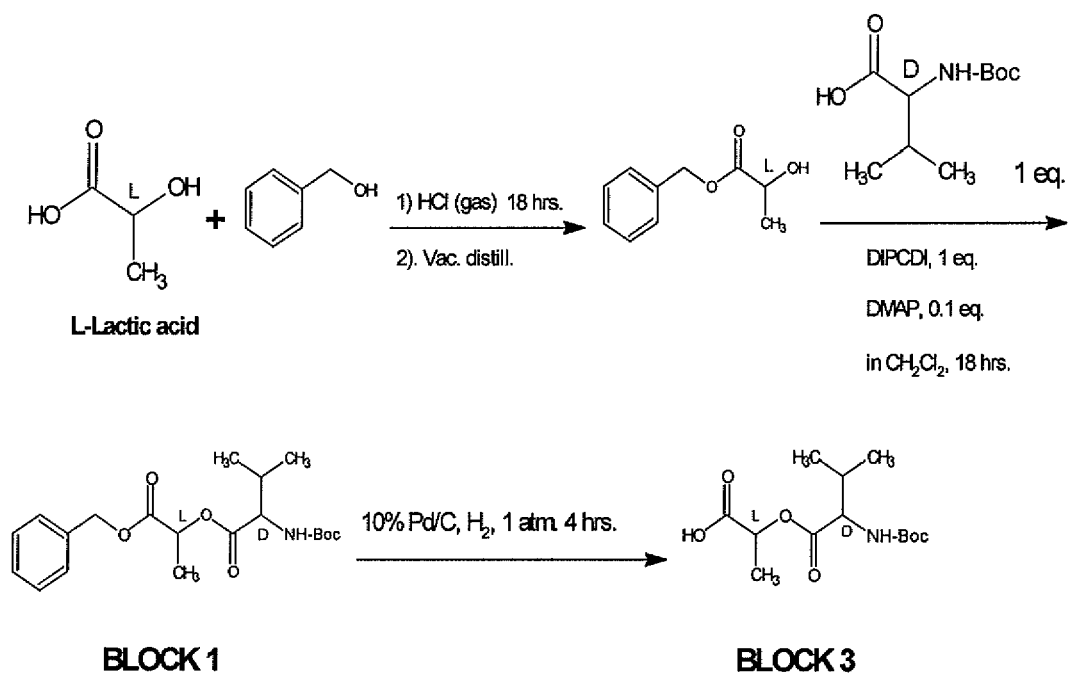
FIG. 2A is a pictorial diagram of an illustrative scheme 1 for the syntheses of block 1 and block 3 in the synthetic sequence that leads to the synthesis of compound I.
Figure 2B:
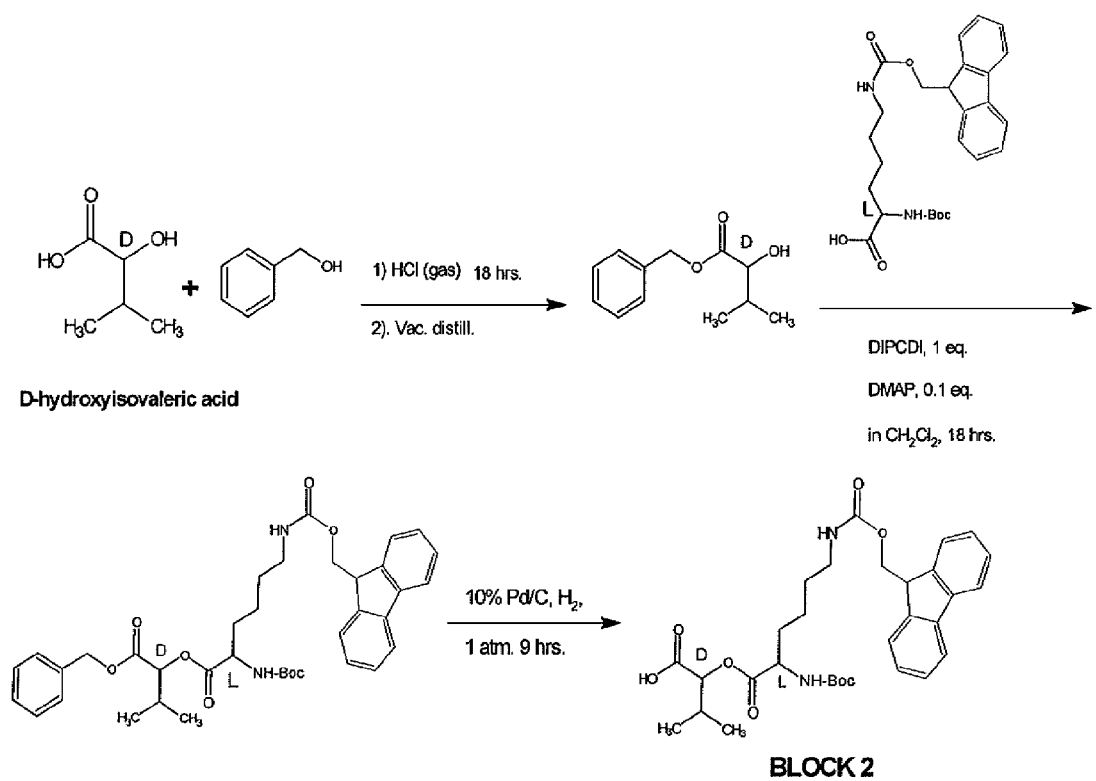
FIG. 2B is a pictorial diagram of an illustrative synthetic scheme 2 for the synthesis of block 2 in the synthetic sequence that leads to the synthesis of compound I.
Figure 2C:
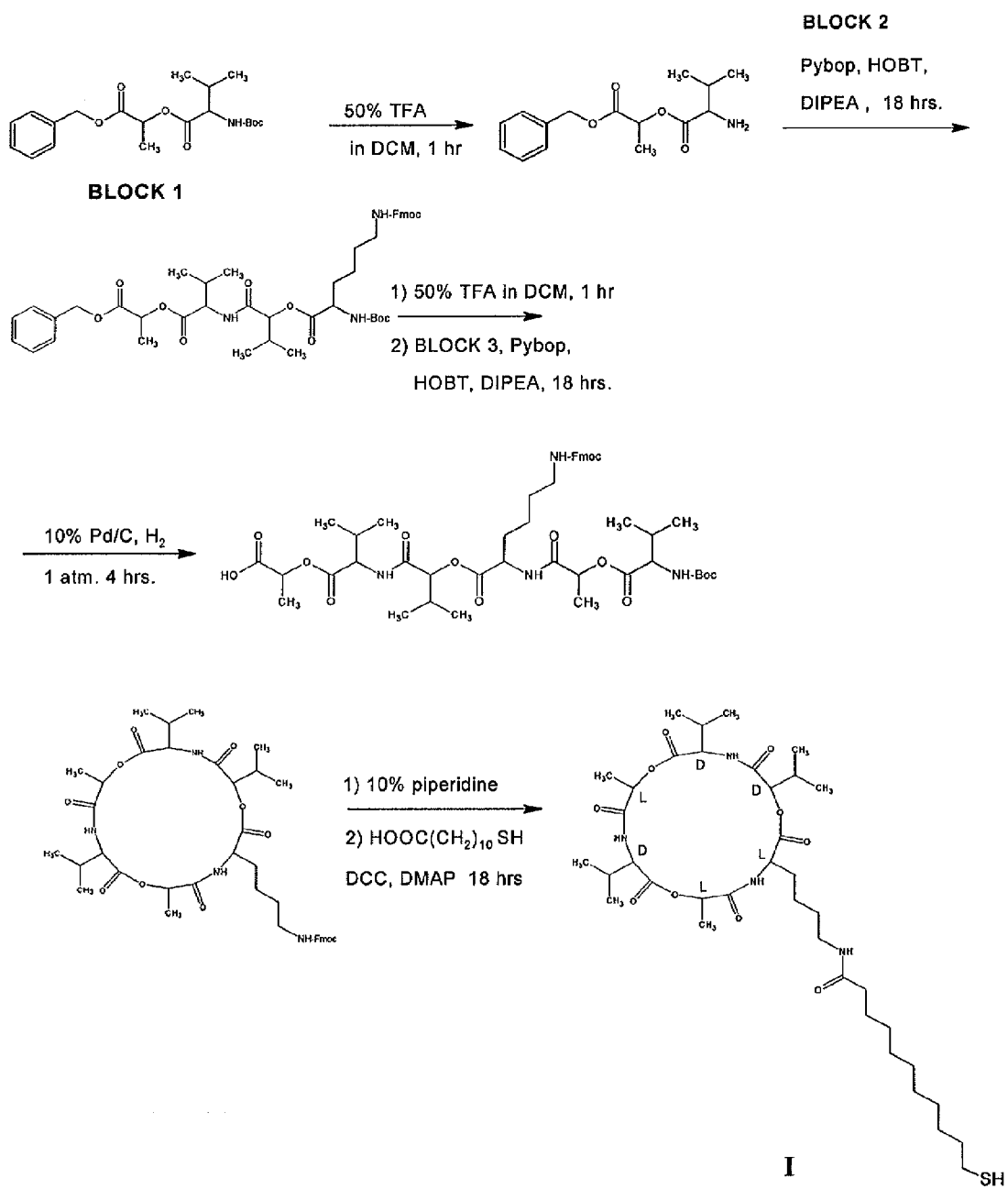
FIG. 2C is a pictorial diagram of an illustrative synthetic scheme 3 in the synthetic sequence that leads to the synthesis of compound I.

The synthetic schemes for target compound I are shown in FIG. 2A-C. Three building blocks were synthesized from the corresponding benzyl-L-lactic acid and Boc-D-Val-OH residue (block 1), D-Hydroxyisovaleric acid and Boc-Lys (Fmoc)-OH residue (block 2), L-lactic acid and Boc-D-Val-OH residue (block 3). These building blocks were coupled sequentially as block 1-block 2-block 3, then cyclized to give cyclic depsipeptide, and finally coupled with 11-mercaptoundecanoic acid to give the title compound I. All of the ester and amide bonds of the depsi-peptide were created in solution. Three types of protecting groups, (t-Butyl (tBu), fluorenyl-methoxycarbonyl (Fmoc), and benzyloxy (BzlO)) were used in this synthesis strategy.

Following is the description of the synthetic scheme 1 presented in FIG. 2A.

(i) Benzyl Ester L-Lactic Acid, (BzlO-L-Lac)

In a round bottom flask, 25.00 g (277.53 mmol) of L-lactic acid was dissolved in 300 mL of anhydrous benzyl alcohol. The solution was saturated with HCl gas and stirred for 18 hrs. at room temperature where upon the solution was dilute with 400 mL $CH_2Cl_2$. The organic layer was washed 3 times with 200 mL 1N KOH, and then with 200 mL 10% citric acid and dried over $Na_2SO_4$. The $CH_2Cl_2$ fraction was then removed under vacuum, 40° C. The benzyl alcohol was removed by vacuum distillation at 35° C. (2.5 mmHg) and the product was collected at 60° C. as a colorless oil, 33.11 g, 66.20% yield. The NMR spectra confirms to the literature (see, Borchardt, M., Dumschat, C., Cammann, K., Knoll, M., *Sens. Actuators, B., B*25, p 721-723 (1995.) $^1$H-NMR (400 MHz, $CDCl_3$), δ 1.42 (dd, J=7.07, 1.01, 3H), 3.08 (d, J=4.80, 1OH), 4.28-4.34 (m, 1H), 5.19 (s, 2H), 7.30-7.38 (m, 5H); $^{13}$C-NMR (100 MHz, $CDCl_3$), δ 20.5 ($CH_3$), 67.0 (CH), 67.3 ($CH_2$), 127.9, 128.4, 128.6, 128.8 (CH—Ar), 135.4 (C—Ar), 175.7 (C=O).

(ii) BzlO-L-Lac-D-Val-NHboc (Block 1)

In a round bottom flask, 10.00 g (46.01 mmol) of Boc-D-Val-OH was dissolved in 200 mL of anhydrous $CH_2Cl_2$. The solution was stirred for 15 min at 0° C., then 7.12 mL (1 eq.) of diisopropylcarbodiimide (DIPCDI) was added followed by adding 0.56 g (0.1 eq.) of 4-dimethylaminopyridine (DMAP). The solution was stirred for 15 min. in ice bath where upon 8.29 g (1 eq.) of L-lactic acid benzyl ester was added. After the solution was stirred at 0° C. for 1 hr, it was then stirred for an additional 17 hrs. at room temperature. The insoluble urea thus formed was filtered off, then the solution was washed thrice with 200 mL saturated $NaHCO_3$, thrice with 200 mL 10% citric acid, once with water and then dried over $Na_2SO_4$. The $CH_2Cl_2$ fraction was then removed under vacuum, 45° C. to yield a clear gum. The product was obtained by column chromatography (hexane: EtOAc: $CH_2Cl_2$ 9:1:1) to yield 16.48 g of a colorless oil, yield 94.39%. $R_f$=0.29 (hexane: EtOAc: $CH_2Cl_2$ 9:1:1); $^1$H-NMR (400 MHz, $CDCl_3$), δ 0.90 (d, J=7.07, 3H), 0.97 (d, J=7.07, 3H), 1.43-1.47 (m, 9H), 1.51 (d, J=7.07, 3H), 2.06-2.09 (m, 1H), 4.27-4.35 (m, 1H), 5.03 (q, J=8.84, 1H), 5.15-5.20 (m, 2H), 7.30-7.40 (m, 5H); $^{13}$C-NMR (100 MHz, $CDCl_3$), δ 17.1 ($CH_3$), 17.6 ($CH_3$), 19.1 ($CH_3$), 28.4 (3×$CH_3$), 31.4 (CH), 58.7 (CH), 67.2 ($CH_2$), 69.3 (CH), 79.8 (C), 128.3, 128.6, 128.7 (CH—Ar) 135.3 (C—Ar), 155.7, 170.2, 171.6 (C=O).

(iii) L-Lac-D-Val-NHboc, (Block 3)

In a round bottom flask, 6.00 g (15.81 mmol) of the BzlO-L-Lac-D-Val-NHboc was dissolved in 100 mL anhydrous $CH_2Cl_2$. The benzyl ester group was removed by hydrogenation reaction using 0.50 g of Pd activated carbon as the catalyst, and gas hydrogen ($H_2$) flowed over for 4 hrs. Then the Pd activated carbon was filtered off and the solution was concentrated under vacuum, 45° C., to yield a light-yellow gum. The product was obtained by column chromatography, the column being a normal phase silica gel column having a particle size of 40 microns and a pore size of 60 Angstroms (hereinafter "column chromatograph"), ($CH_2Cl_2$:MeOH 85:15) to yield 4.11 g of a white amorphous solid, yield 89.93%. $R_f$=0.4 ($CH_2Cl_2$:MeOH 85:15); $^1$H-NMR (400 MHz, $CD_3OD$), δ 0.96 (d, J=7.07, 3H), 1.00 (d, J=7.07, 3H), 1.43-1.51 (m, 12H), 2.11-2.22 (m, 1H), 4.10 (d, J=5.81, 1H), 5.05-5.10 (m, 1H); $^{13}$C-NMR (100 MHz, $CD_3OD$), δ 16.5 ($CH_3$), 17.4 ($CH_3$), 18.6 ($CH_3$), 27.6 ($CH_3$), 27.8 (2×$CH_3$), 30.9 (CH), 59.7 (CH), 69.4 (CH), 79.6 (C), 157.2, 172.1, 172.8 (C=O).

Following is the description of the synthetic scheme 2 presented in FIG. 2B.

(i) D-hydroxyisovaleric acid benzyl ester. (BzlO-D-Hyisoval)

This compound was prepared in the same manner as L-lactic acid benzyl ester using 9.80 g (82.96 mmol) of D-hydroxyisovaleric acid. The product was recovered as a colorless oil, 10.12 g, 58.58% yield. The NMR spectra confirms to the literature (see, Liu, D., Meyerhoff, M. E., Goldberg, H. D., Brown, R. B., *Anal. Chim. Acta.,* 274, p 37-46 (1993); Pranitis, D. M., Meyerhoff, M. E., *Anal. Chem.,* 59, 2345-2350 (1987.) $^1$H-NMR (400 MHz, $CDCl_3$), δ 0.83 (d, J=7.07, 3H), 1.00 (d, J=7.07, 3H), 2.07-2.13 (m, 1H), 2.76 (d, J=5.81, 1OH), 4.04-4.13 (m, 1H), 5.15-5.28 (m, 2H), 7.25-7.51 (m, 5H); $^{13}$C-NMR (100 MHz, $CDCl_3$), δ 16.0 ($CH_3$), 19.0 ($CH_3$), 32.3 (CH), 67.5 ($CH_2$), 75.2 (CH), 127.8, 128.0, 128.6, 128.7, 128.8 (CH—Ar), 135.4 (C—Ar), 175.0 (C=O).

(ii) BzlO-D-Hyisoval-L-Lys(Fmoc)-NHboc.

In a round bottom flask, 10.00 g (21.34 mmol) of Boc-Lys (Fmoc)-OH was dissolved in 200 mL of anhydrous $CH_2Cl_2$. The solution was stirred for 15 min at 0° C., then 3.3 mL (1 eq.) of DIPCDI was added followed by adding 0.26 g (0.1 eq.) of DMAP. The solution was stirred for 15 min. in ice bath where upon 4.44 g (1 eq.) of BzlO-D-hyisoval was added. After the solution was stirred at 0° C. for 1 hr, it was then stirred for an additional 17 hrs. at room temperature. The insoluble urea thus formed was filtered off, then the solution was washed thrice with 150 mL saturated $NaHCO_3$, thrice with 150 mL 10% citric acid, once with water and then dried over $Na_2SO_4$. The $CH_2Cl_2$ fraction was then removed under vacuum, 45° C. to yield a white amorphous crystal. The product was purified by recrystallization using dichloromethane and cold ether to yield a white solid, and followed by column chromatography (hexane:EtOAc 7:3) to yield 9.87 g of a white crystal, yield 70.20%. $R_f$=0.31 (hexane:EtOAc 7:3); $^1$H-NMR (400 MHz, $CDCl_3$), δ 0.93 (d, J=7.07, 3H), 0.97 (d, J=7.07, 3H), 1.23-1.59 (m, 13H), 1.61-1.76 (m, 1H), 1.76-1.93 (m, 1H), 2.19-2.33 (m, 1H), 2.94-3.27 (m, 2H), 4.17-4.25 (dd, J=7.07, 6.82, 1H), 4.35-4.43 (m, 2H), 4.87-4.98 (m, 2H), 5.02-5.25 (m, 2H), 7.25-7.45 (m, 9H), 7.59 (d, J=7.58, 2H), 7.75 (d, J=7.58, 2H); $^{13}$C-NMR (100 MHz, CDCl$_3$), δ 17.3 (CH$_3$), 19.0 (CH$_3$), 22.5 (CH$_2$), 28.5 (3×CH$_3$), 29.5 (CH$_2$), 30.3 (CH), 32.4 (CH$_2$), 40.7 (CH$_2$), 47.4 (CH), 53.7 (CH), 66.7 (CH$_2$), 67.2 (CH$_2$), 77.4 (CH), 80.3 (C), 120.1, 125.2, 127.2, 127.8, 128.5, 128.6, 128.8 (CH—Ar), 135.4, 141.5, 144.2 (C—Ar), 155.5, 156.6, 169.3, 172.3 (C═O).

(iii) D-Hyisoval-L-Lys(Fmoc)-NHboc (Block 2)

In a round bottom flask, 9.44 g (14.33 mmol) of the BzlO-D-hyisoval-L-Lys(Fmoc)-NHboc was dissolved in 200 mL anhydrous CH$_2$Cl$_2$. The benzyl ester group was removed by hydrogenation reaction using 1 g of Pd activated carbon as the catalyst, and gas hydrogen (H$_2$) flowed over for 9 hrs. Then the Pd activated carbon was filtered off and the solution was concentrated under vacuum, 45° C., to yield a white amorphous crystal. The product was obtained by column chromatography (CH$_2$Cl$_2$:MeOH 90:10) to yield 7.72 g of a white amorphous solid, yield 94.74%. R$_f$=0.6 (90:10 CH$_2$Cl$_2$:MeOH); $^1$H-NMR (400 MHz, CDCl$_3$), δ 0.99 (d, J=7.07, 3H), 1.00 (d, J=7.07, 3H), 1.25-1.55 (m, 13H), 1.61-1.76 (m, 1H), 1.76-1.95 (m, 1H), 2.19-2.35 (m, 1H), 2.92-3.25 (m, 2H), 4.11-4.25 (m, 1H), 4.33-4.48 (m, 2H), 4.85-4.98 (m, 1H), 5.18-5.32 (m, 1H), 7.24-7.42 (m, 4H), 7.57 (d, J=7.58, 2H), 7.74 (d, J=7.58, 2H), 10.0 (s-br, 1H); $^{13}$C-NMR (100 MHz, CDCl$_3$), δ 17.1 (CH$_3$), 19.0 (CH$_3$), 22.5 (CH$_2$), 28.3 (CH$_3$), 28.5 (2×CH$_3$), 29.5 (CH$_2$), 30.1 (CH), 32.1 (CH$_2$), 40.7 (CH$_2$), 47.3 (CH), 53.6 (CH), 66.7 (CH$_2$), 77.4 (CH), 80.3 (C), 120.1, 125.0, 125.2, 127.2, 127.8, 127.9 (CH—Ar), 141.4, 144.0 (C—Ar), 155.8, 156.8, 172.4, 173.0 (C═O).

Following is the description of the synthetic scheme 3 presented in FIG. 2C.

(i) BzlO-L-Lac-D-Val-NH$_2$

In a round bottom flask, 5.10 g (13.44 mmol) of block 1 was dissolved in 50 mL anhydrous CH$_2$Cl$_2$, and then deprotected with 50% trifloroacetic acid (TFA, 50 mL) for 1 hr. The CH$_2$Cl$_2$ and TFA were then removed under vacuum, 35° C. 1 mL of CH$_2$Cl$_2$ and 2 mL of toluene were added thrice to the residue, and then removed thrice under vacuum, to yield a brown gum residue in quantitative yield. $^1$H-NMR (400 MHz, CDCl$_3$), δ 1.02-1.10 (dd, J=7.07, 14.14, 6H), 1.50 (d, J=7.07, 3H), 2.30-2.41 (m, 1H), 3.96-4.02 (d-br, J=3.03, 1H), 5.13 (q, J=8.84, 1H), 5.18-5.24 (m, 2H), 7.25-7.38 (m, 5H); $^{13}$C-NMR (100 MHz, CDCl$_3$), δ 16.7 (CH$_3$), 17.5 (CH$_3$), 17.9 (CH$_3$), 29.9 (CH), 58.4 (CH), 67.5 (CH$_2$), 70.5 (CH), 128.4, 128.5, 128.7, 128.7, 129.2 (CH—Ar) 135.0 (C—Ar), 168.1, 169.7 (C═O).

(ii) BzlO-L-Lac-D-Val-D-Hyisoval-L-Lys(Fmoc)-NHboc

In a round bottom flask 7.60 g (13.36 mmol) of D-hyisoval-L-Lys(Fmoc)-NHboc (block 2) was dissolved in 150 mL of anhydrous CH$_2$Cl$_2$. The solution was stirred for 5 min at room temperature, then 6.96 g (1 eq.) of benzotriazole-1-yl-oxy-tris-pyrrolidino-phosphonium hexafluorophosphate (PyBOP), 2.05 g (1 eq.) 1-hydroxybenzo-triazole hydrate (HOBT), and 23.3 mL (10 eq.) of diisopropylethylamine (DIPEA) were added. The solution was stirred for 5 min. where upon the deprotecting block I in dry CH$_2$Cl$_2$ was added. This solution mixture was then stirred for an additional 18 hrs at room temperature. The insoluble urea thus formed was filtered off, then the solution was washed thrice with 150 mL saturated NaHCO$_3$, thrice with 150 mL 10% citric acid, once with water and then dried over Na$_2$SO$_4$. The CH$_2$Cl$_2$ was then removed under vacuum, 45° C. to yield a light brown crystal. The product was purified by column chromatography (hexane:EtOAc 62:38) to yield 9.81 g of a white crystal, yield 88.44%. R$_f$=0.30 (hexane:EtOAc 62:38); $^1$H-NMR (400 MHz, CDCl$_3$), δ 0.96-0.99 (m, 12H), 1.26-1.52 (m, 16H), 1.62-1.78 (m, 1H), 1.78-1.93 (m, 1H), 2.24-2.40 (m, 2H), 2.95-3.22 (m, 2H), 4.19 (m, 1H), 4.28 (m, 1H), 4.33-4.42 (m, 2H), 4.52-4.60 (m, 1H), 5.04-5.21 (m, 5H), 5.32 (d, J=7.33, 1NH), 6.81 (d, J=8.08, 1NH), 7.26-7.35 (m, 7H), 7.38 (t, J=7.58, 2H), 7.58 (d, J=7.58, 2H), 7.74 (d, J=7.58, 2H); $^{13}$C-NMR (100 MHz, CDCl$_3$), δ 16.9 (CH$_3$), 17.0 (CH$_3$), 18.1 (CH$_3$), 18.9 (CH$_3$), 19.1 (CH$_3$), 22.6 (CH$_2$), 28.3 (3×CH$_3$), 29.5 (CH$_2$), 30.5 (CH), 30.8 (CH), 31.5 (CH$_2$), 40.4 (CH$_2$), 47.3 (CH), 53.9 (CH), 57.5 (CH), 66.6 (CH$_2$), 67.2 (CH$_2$), 69.4 (CH), 78.7 (C), 80.1 (CH), 120.0, 125.1, 127.1, 127.7, 128.2, 128.5, 128.7, (CH—Ar), 135.2, 141.3, 144.0, 144.1 (C—Ar), 155.6, 156.7, 169.2, 170.1, 170.7, 171.9 (C═O).

(iii) BzlO-L-Lac-D-Val-D-Hyisoval-L-Lys(Fmoc)-NH$_2$

In a round bottom flask, 9.30 g (11.20 mmol) of the BzlO-L-Lac-D-Val-D-hyisoval-L-Lys(Fmoc)-NHboc was dissolved in 75 mL anhydrous CH$_2$Cl$_2$, and then deprotected with 50% trifloroacetic acid (TFA, 75 mL) for 1 hr. The CH$_2$Cl$_2$ and TFA were then removed under vacuum, 35° C. Then, 1 mL of CH$_2$Cl$_2$ and 2 mL of toluene were added thrice to the residue, and then removed thrice under vacuum, to yield a brown gum residue in quantitative yield.

(iv) BzlO-L-Lac-D-Val-D-Hyisoval-L-Lys(Fmoc)-L-Lac-D-Val-NHboc (Linear Depsi Peptide)

In a round bottom flask 3.73 g (12.89 mmol, 1.15 eq.) of L-Lac-D-Val-NHboc, (block 3) was dissolved in 200 mL of anhydrous CH$_2$Cl$_2$. The solution was stirred for 5 min at room temperature, then 6.71 g (1.15 eq.) of PyBOP, 1.97 g (1.15 eq.) of HOBT, and 19.5 mL (10 eq.) of DIPEA were added. The solution was stirred for 5 min. where upon the BzlO-L-Lac-D-Val-D-hyisoval-L-Lys(Fmoc)-NH$_2$ in anhydrous CH$_2$Cl$_2$ was added. This solution mixture was then stirred for an additional 18 hrs at room temperature. The insoluble urea thus formed was filtered off, then the solution was washed thrice with 200 mL saturated NaHCO$_3$, thrice with 200 mL 10% citric acid, once with water and then dried over Na$_2$SO$_4$. The CH$_2$Cl$_2$ fraction was then removed under vacuum, 45° C. to yield a light brown crystal. The product was purified by column chromatography (CH$_2$Cl$_2$:EtOAc:hexane 2:3:5) to yield 5.25 g of a white crystal, yield 46.79%. R$_f$=0.40 (CH$_2$Cl$_2$:EtOAc:hexane 2:3:5); $^1$H-NMR (400 MHz, CDCl$_3$), δ 0.92-1.05 (m, 18H), 1.20-1.31 (m, 2H), 1.31-1.58 (m, 17H), 1.88-2.10 (m, 3H), 2.25-2.43 (m, 2H), 3.04-3.29 (m, 2H), 3.94 (t, J=6.82, 1H), 4.17-4.23 (m, 1H), 4.32-4.43 (m, 3H), 4.44-4.50 (m, 1H), 5.03 (d, J=3.54, 1H), 5.10-5.25 (m, 5H), 5.38-5.43 (m, 1NH), 7.26-7.35 (m, 7H), 7.39 (t, J=7.58, 2H), 7.51 (d-br, J=8.08, 1NH), 7.58 (d, J=7.58, 2H), 7.75 (d, J=7.58, 2H); $^{13}$C-NMR (100 MHz, CDCl$_3$), δ 16.8 (CH$_3$), 16.9 (CH$_3$), 17.4 (CH$_3$), 18.6 (CH$_3$), 18.7 (CH$_3$), 19.0 (CH$_3$), 19.1 (CH$_3$), 19.3 (CH$_3$), 23.0 (CH$_2$), 28.4 (3×CH$_3$), 29.4 (CH$_2$), 30.3 (CH), 30.3 (CH), 31.7 (CH), 32.0 (CH$_2$), 40.5 (CH$_2$), 47.3 (CH), 53.7 (CH), 58.1 (CH), 60.0 (CH), 66.7 (CH$_2$), 67.1 (CH$_2$), 69.2 (CH), 70.1 (CH), 78.9 (CH), 80.7 (C), 120.1, 125.2, 127.1, 127.8, 128.3, 128.4, 128.6 (CH—Ar), 135.4, 141.4, 144.1 (C—Ar), 156.4, 156.6, 169.6, 170.4, 170.6, 171.2, 171.4, 171.9 (C═O).

(v) L-Lac-D-Val-D-Hyisoval-L-Lys(Fmoc)-L-Lac-D-Val-NHboc

In a round bottom flask, 5.1 g (5.1 mmol) of the BzlO-L-Lac-D-Val-D-hyisoval-L-Lys(Fmoc)-L-Lac-D-Val-NHboc was dissolved in 100 mL anhydrous CH$_2$Cl$_2$. The benzyl ester group was removed by hydrogenation reaction using 0.5 g of Pd activated carbon as the catalyst, and gas hydrogen (H$_2$) flowed over for 4 hrs. Then the Pd activated carbon was filtered off and the solution was concentrated under vacuum, 45° C., to yield a white crystal. The product was obtained by column chromatography (CH$_2$Cl$_2$:MeOH 80:20) to yield 4.5 g of a white amorphous solid, yield 97.0%. R$_f$=0.5 (CH$_2$Cl$_2$:MeOH 80:20); $^1$H-NMR (400 MHz, CD$_3$OD), δ 0.91-1.07

(m, 12H), 1.36-1.51 (m, 19H), 1.75-1.89 (m, 1H), 1.89-2.03 (m, 1H), 2.06-2.31 (m, 3H), 3.05-3.16 (m, 2H), 3.98-4.09 (m, 1H), 4.13-4.23 (m, 1H), 4.27-4.35 (m, 1H), 4.36-4.58 (m, 3H), 4.83 (d, J=5.56, 1H), 5.01-5.10 (m, 1H), 5.14-5.28 (m, 1H), 7.30 (t, J=7.58, 2H), 7.38 (t, J=7.58, 2H), 7.63 (d, J=7.58, 2H), 7.77 (d, J=7.58, 2H); $^{13}$C-NMR (100 MHz, CD$_3$OD), δ 17.8 (CH$_3$), 18.4 (CH$_3$), 19.0 (CH$_3$), 19.6 (CH$_3$), 20.0 (CH$_3$), 24.4 (CH$_2$), 29.2 (3×CH$_3$), 30.7 (CH$_2$), 32.1 (CH), 32.2 (CH), 32.3 (CH), 32.5 (CH$_2$), 41.8 (CH$_2$), 48.9 (CH), 54.3 (CH), 59.5 (CH), 61.3 (CH), 68.0 (CH$_2$), 71.2 (CH), 71.9 (CH), 80.4 (CH), 81.0 (C), 121.3, 126.6, 128.6, 129.2 (CH—Ar), 143.0, 145.7 (C—Ar), 158.7, 159.3, 172.3, 173.0, 173.3 173.4, 174.5 (C═O).

(vi) Cyclo-L-Lac-D-Val-D-Hyisoval-L-Lys(Fmoc)-L-Lac-D-Val (Cyclic Depsi-Peptide)

In a round bottom flask, 1.1 g (1.2 mmol) of the L-Lac-D-Val-D-hyisoval-L-Lys(Fmoc)-L-Lac-D-Val-NHboc was dissolved in 75 mL anhydrous CH$_2$Cl$_2$, and then deprotected with 50% trifloroacetic acid (TFA, 75 mL) for 1 hr. The CH$_2$Cl$_2$ and TFA were then removed under vacuum, 35° C. Then, 1 mL of CH$_2$Cl$_2$ and 2 mL of toluene were added thrice to the residue, and then removed thrice under vacuum, to yield L-Lac-D-Val-D-hyisoval-L-Lys(Fmoc)-L-Lac-D-Val-NH$_2$ (a brown gum residue) in quantitative yield.

In a round bottom flask L-Lac-D-Val-D-hyisoval-L-Lys (Fmoc)-L-Lac-D-Val-NH$_2$ was dissolved in 500 mL of anhydrous DMF. The solution was stirred for 15 min at 0° C., where upon 2.1 mL (10 eq.) of DIPEA, 0.60 g (1.3 eq.) of O-(7-Azabenzotriazole-1-yl)-N,N,N',N'-tetramethyluronium hexafluorophosphate (HATU), and 0.21 g (1.3 eq.) 1-Hydroxy-7-azabenzotriazole (HOAT) were added. The solution was continuously stirred at 0° C. for 8 hours, and then it was allowed to be stirred for an additional 1 hour at room temperature. The DMF was then removed under vacuum, 45° C. to yield a brown gum. After that, 200 mL of CH$_2$Cl$_2$ was added to precipitate the insoluble urea from the solution. The insoluble compound thus formed was filtered off, then the solution was washed thrice with 200 mL saturated NaHCO$_3$, thrice with 200 mL 10% citric acid, once with water and then dried over Na$_2$SO$_4$. The CH$_2$Cl$_2$ fraction was then removed under vacuum, 45° C. to yield an off-white crystal. The product was purified by column chromatography (CH$_2$Cl$_2$:EtOAc:hexane 2:4:4) to yield 0.59 g of a white crystal, yield 61.65%. R$_f$=0.35 (CH$_2$Cl$_2$:EtOAc:hexane 2:4:4); $^1$H-NMR (400 MHz, CDCl$_3$), δ 0.88-1.04 (m, 18H), 1.24-1.41 (m, 4H), 1.41-1.65 (m, 6H), 1.88-2.05 (m, 3H), 2.15-2.39 (m, 2H), 3.01-3.37 (m, 2H), 4.10-4.28 (m, 2H), 4.28-4.50 (m, 3H), 4.63-4.75 (m, 1H), 5.05-5.25 (m, 3H), 5.25-5.40 (m, 1H), 6.64 (d, J=8.59, 1NH), 6.75-6.89 (m, 1NH), 7.13-7.24 (m, 1NH), 7.30 (t, J=7.58, 2H), 7.40 (t, J=7.58, 2H), 7.53-7.62 (m, 2H), 7.76 (d, J=7.58, 2H); $^{13}$C-NMR (100 MHz, CDCl$_3$), δ 15:5 (CH$_3$), 17.4 (CH$_3$), 17.8 (CH$_3$), 18.0 (CH$_3$), 18.6 (CH$_3$), 19.0 (CH$_3$), 19.1 (CH$_3$), 19.3 (CH$_3$), 23.1 (CH$_2$), 29.4 (CH$_2$), 29.6 (CH), 30.1 (CH$_2$), 30.8 (CH), 31.3 (CH), 40.2 (CH$_2$), 47.4 (CH), 53.4 (CH), 56.7 (CH), 59.6 (CH), 66.7 (CH$_2$), 69.9 (CH), 71.8 (CH), 79.5 (CH), 120.2, 125.1, 127.2, 127.9 (CH—Ar), 141.5, 144.1 (C—Ar), 156.8, 169.1, 170.6, 170.7, 171.0, 172.7 (C═O). EIS MS m/z calcd. for C$_{42}$H$_{57}$N$_4$O$_1$ (MH$^+$) 793.9 found 793.9.

(vii) Cyclo-L-Lac-D-Val-D-Hyisoval-L-Lys(NH$_2$)-L-Lac-D-Val

In a round bottom flask, 0.8 g (1.01 mmol) of cyclo-L-Lac-D-Val-D-hyisoval-L-Lys(Fmoc)-L-Lac-D-Val was dissolved in 50 mL solution of 10% piperidine in CH$_2$Cl$_2$ for 20 min. The CH$_2$Cl$_2$ and piperidine were then removed under vacuum, 35° C. to yield a brown gum residue. Then, 1 mL of CH$_2$Cl$_2$ and 2 mL of toluene were added thrice to the residue, and removed thrice under vacuum. The product was purified by column chromatography (CH$_2$Cl$_2$:MeOH 30:1) to yield 0.42 g of off-white crystal, yield 72.41%. R$_f$=0.25 (CH$_2$Cl$_2$: MeOH 30:1); $^1$H-NMR (400 MHz, CDCl$_3$), δ 0.87-1.04 (m, 18H), 1.23-1.57 (m, 8H), 1.73-1.90 (m, 2H), 1.95-2.09 (m, 2H), 2.09-2.19 (m, 1H), 2.19-2.39 (m, 2H), 3.18-3.34 (m, 2H), 3.38 (d, J=3.03, 1H), 4.41-4.54 (m, 1H), 4.54-4.70 (m, 2H), 5.15-5.38 (m, 2H), 6.92-7.02 (m, 1NH), 7.25-7.32 (m, 1NH), 7.30-7.42 (m, 1NH), 7.55-7.74 (m, 1NH); $^{13}$C-NMR (100 MHz, CDCl$_3$), δ 15.9 (CH$_3$), 17.9 (CH$_3$), 18.0 (CH$_3$), 18.0 (CH$_3$), 19.1 (CH$_3$), 19.3 (CH$_3$), 28.0 (CH$_2$), 28.9 (CH$_2$), 30.5 (CH), 30.9 (CH), 31.4 (CH$_2$), 31.9 (CH), 42.1 (CH$_2$), 52.0 (CH), 53.6 (CH), 57.3 (CH), 71.1 (CH), 71.4 (CH), 76.4 (CH), 169.6, 170.4, 170.8, 171.2, 174.4, 175.3 (C═O).

(viii) Compound I

In a round bottom flask, 0.40 g (0.70 mmol) of cyclo-L-Lac-D-Val-D-hyisoval-L-Lys(NH$_2$)-L-Lac-D-Val was dissolved in 20 mL of anhydrous CH$_2$Cl$_2$. The solution was stirred for 10 min at 0° C., then 0.1446 g (1 eq.) of 1,3-dicyclohexylcarbodiimide (DCC) was added followed by adding 0.0086 g (0.1 eq.) DMAP. The solution was stirred for 10 min. in ice bath where upon 0.1611 g (1 eq.) of 11-mercaptoundecanoic acid was added. After the solution was stirred at 0° C. for 1 hr, it was then stirred for an additional 23 hrs. at room temperature. The insoluble urea thus formed was filtered off, then the CH$_2$Cl$_2$ was removed under vacuum, 45° C. to yield an off-white gum. The product was obtained by column chromatography (CH$_2$Cl$_2$:MeOH 60:1) to yield 0.38 g of an off-white oil, yield 70.37%. R$_f$=0.21 (CH$_2$Cl$_2$:MeOH 60:1); $^1$H-NMR (400 MHz, CDCl$_3$), δ 0.77 (d, J=7.07, 3H), 0.92 (d, J=7.07, 3H), 0.93-1.05 (m, 12H), 1.21-1.42 (m, 20H), 1.45-1.57 (m, 8H), 1.57-1.72 (m, 6H), 1.75-1.98 (m, 2H), 1.98-2.16 (m, 2H), 2.16-2.36 (m, 3H), 2.44 (t, J=7.58, 2H), 2.52 (q, J=7.33, 2H), 3.18-3.33 (m, 2H), 4.41-4.51 (m, 1H), 4.67-4.77 (m, 1H), 4.78-4.85 (m, 1H), 4.92 (d, J=5.31, 1H), 5.18-5.31 (m, 2H), 6.92 (d, J=8.59, 1NH), 7.08-7.15 (m, 1NH), 7.25 (d, J=9.09, 1NH), 7.60 (d, J=6.06, 1NH); $^{13}$C-NMR (100 MHz, CDCl$_3$), δ 17.5 (CH$_3$), 17.9 (CH$_3$), 18.0 (CH$_3$), 18.8 (CH$_3$), 19.1 (CH$_3$), 19.2 (CH$_3$), 25.1 (CH$_2$), 25.7 (CH$_2$), 25.8 (CH$_2$), 28.0 (CH$_2$), 28.9 (CH$_2$), 29.1 (CH$_2$), 29.2 (CH$_2$), 29.6 (CH$_2$), 30.4 (CH), 30.6 (CH), 31.5 (CH), 34.1 (CH$_2$), 34.3 (CH$_2$), 42.1 (CH$_2$), 51.7 (CH), 56.6 (CH), 57.1 (CH), 71.3 (CH), 71.5 (CH), 78.1 (CH), 169.6, 169.7, 169.9, 170.5, 170.9, 173.0, 175.3 (C═O). EIS MS m/z calcd. for C$_{38}$H$_{66}$N$_4$O$_{10}$S (M$^+$) 771.0 found 771.8.

Example 2

Preparation and Characterization of SAMs

Gold slides were purchased from Evaporated Metal Films (EMF, Ithaca, N.Y.). The slides have dimensions of 25 mm×75 mm×1 mm with cut edges, fabricated on a float glass substrate, coated with 50 Å of chromium followed by 100 Å of gold. The substrates were cut in different sizes depending to the experimental needs. The slides were cleaned in piranha solution (70% concentrated sulfuric acid and 30% hydrogen peroxide) for 15 minutes, rinsed with water and ethanol, and dried with nitrogen before use. SAMs of the compound I were prepared by immersing a clean gold slide into a 1-3 mM solution of the thiol in ethanol for up to 48 hours. The SAMs were rinsed with ethanol and dried with nitrogen gas before use.

Contact angle measurements were obtained with a Rame-Hart Model 100-00 Goniometer. Drops of water (1 μL) were deposited with a micropipette and the sessile drop contact angle was measured. The average of at least three measurements from three different samples was obtained.

Thickness measurements were determined with a manual photoelectric Rudolf 439L633P ellipsometer (Rudolph Instruments, Fairfield N.J.). The change in polarization state of light reflected from the surface was measured at 70° angle of incidence using a HeNe laser (632.8 nm) as the source. The thickness of the film was calculated, using the manufacturers software, assuming values for the extinction coefficient and refractive index of the samples to be 0 and 1.47, respectively. The values reported here are the average values obtained from at least three different samples.

IR spectra were obtained with a Nexus FT-IR spectrometer equipped with a ThermoNicolet grazing angle accessory and a liquid-nitrogen cooled MCTA detector. The IR beam was incident at 75 degree on the gold substrates. The optical path was purged with nitrogen gas before and during data acquisition. IR spectra were obtained by collecting 64 scans, with a 4 cm$^{-1}$ resolution, from 4000 to 800 cm$^{-1}$. A clean gold substrate was used as a background before the acquisition of each spectrum.

Impedance measurements were performed with the same three-electrode setup used for cyclic voltammetry. A 1255-HF frequency response analyzer was used in combination with the EG&G Princeton Applied Research Potentiostat/Galvanostat. Impedance measurements were collected with a background electrolyte solution of 0.1 M tetraethylammonium chloride and titrated with 0.1 M solutions of metal chlorides (MCl, M=Na$^+$, K$^+$, Li$^+$, NH$_4^+$). The electrolyte solution was bubbled with nitrogen at least 5 minutes before data acquisition. During the measurements, a constant flow of nitrogen was maintained. The impedance plots were obtained in a frequency range of 10 kHz to 0.1 Hz, at an applied dc voltage of −0.5 V vs Ag/AgCl, with an AC amplitude of 5 mV. At least twenty-five (25) frequencies were used for each measurement and the impedance data was fitted to an equivalent circuit using the LEVMRUN software package for complex non-linear least square calculations. (See, Macdonald, R., *CNLS Immitance, Inversion, and Simulation Fitting Programs for Windows and MS-DOS LEVM Manual* 8.0, University of North Carolina: Chapel Hill, N.C. (2003), the entire teaching of which is incorporated herein by reference.)

Molecular modeling was preformed on a Dell Precision PWS 670 running Windows XP using the Molecular Operating Environment (MOE) version 2004.03 package (Chemical Computing Group Inc., Montreal, Quebec, Canada). The energy minimized structure of a target compound was calculated using two different force fields for comparative purposes, namely, AMBER94 and MMFF94. Calculations with each force field were carried out with a dielectric of 80 (aqueous environment). Before each conformation calculation the partial charges on the molecule were calculated using the corresponding force field. A stochastic conformational search for the equilibrium geometry followed by a dynamics simulation using the NVT (constant particle number N, constant volume V and constant temperature T) statistical ensemble. The dynamics simulation was performed for 20 ps, heating the structure to 400 K, equilibrated at 310 K and cooled to 290 K in the dynamics thermal cycle at a rate of 10 K/ps. The lowest energy structure obtained from these dynamics calculations was then minimized again. For all the calculations performed, the dynamic simulation resulted in a geometry that was either equal to, or lower in energy than the result obtained from the stochastic search. Host—guest calculations were performed by introducing an ion into the centre of the host structure. These systems were minimized, a dynamic simulation was performed and then the result minimized again as previously described. A stochastic conformational search was not carried out for the host guest systems since the random starting coordinates generally places the ion at distance beyond the influence of the host molecules.

Although the invention has been described with respect to various embodiments, it should be realized that this invention is also capable of a wide variety of further and other embodiments according to the scope and the breadth of the claims.

What is claimed is:

1. A compound of Formula (I)

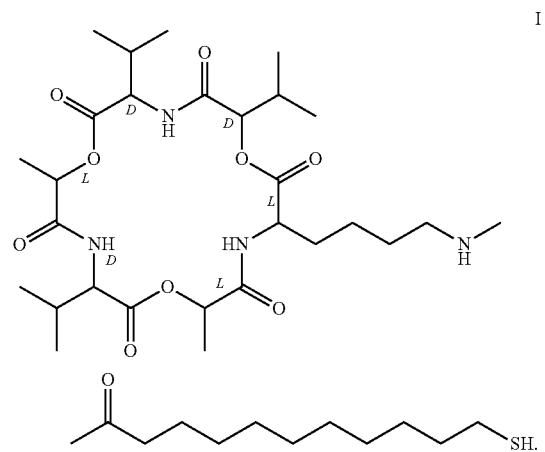

2. A process of making the compound of claim 1 comprising:

(1) a step for converting the compound of Formula (A)

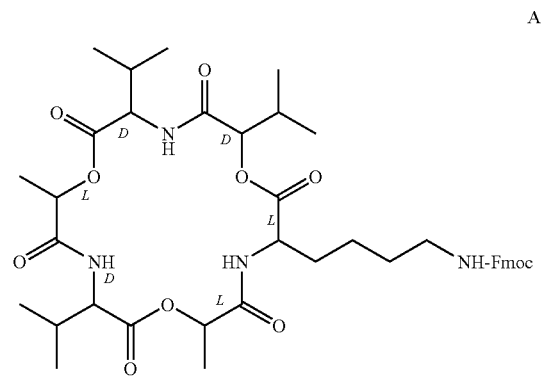

into the compound of Formula (B)

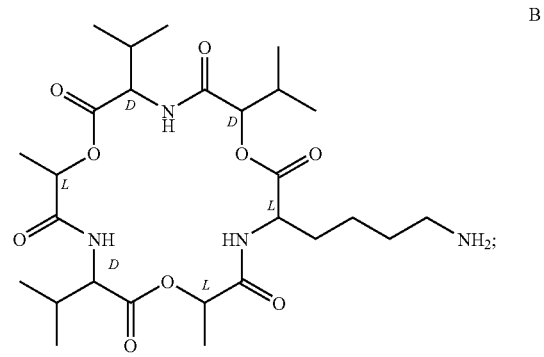

and (2) a step for coupling the compound of Formula (B) with 11-mercaptoundecanoic acid to yield the compound of claim 1.

3. The process of claim 2 further comprising a step for converting the compound of Formula (C) into the compound of Formula (A)
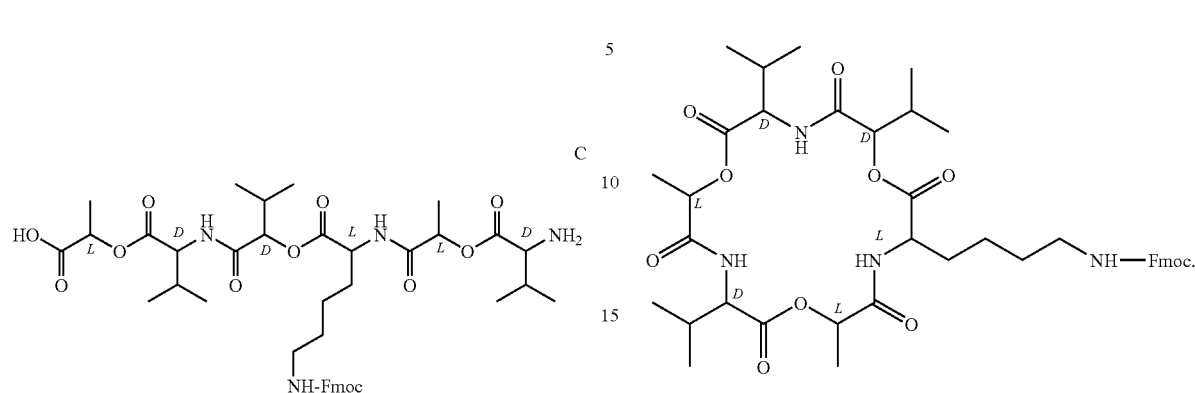
4. The process of claim 3 further comprising the step for removing the t-Butyloxycarbonyl group from the compound of Formula (D)
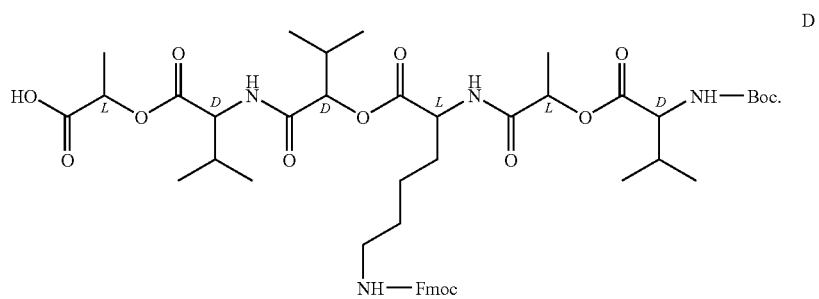
5. The process of claim 4 further comprising a step for converting the compound of Formula (E)
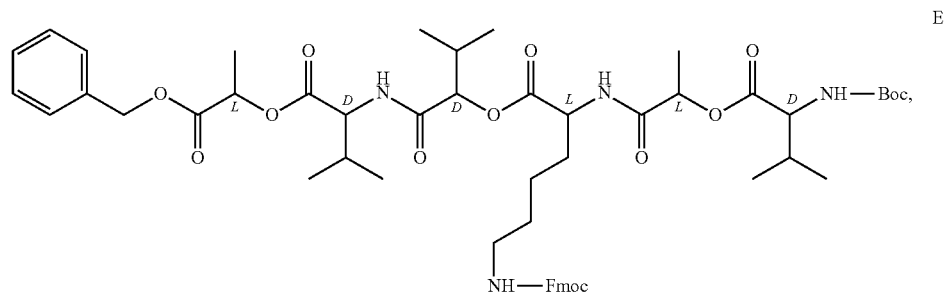

into the compound of Formula (D)

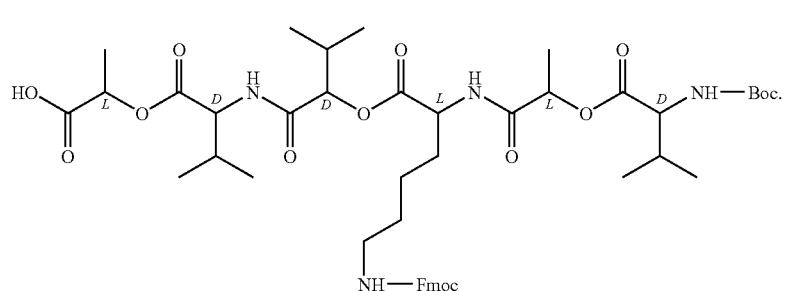

6. The process of claim 5 further comprising the step for coupling the compound of formula (F)

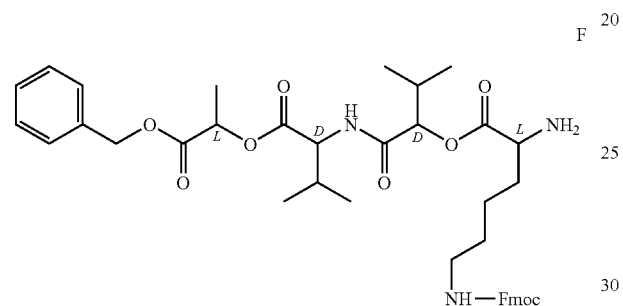

with the compound of Formula (G)

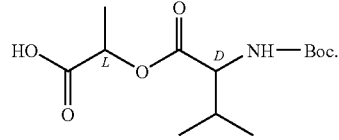

7. The process of claim 6 further comprising the step for removing the t-Butyloxycarbonyl group from the compound of Formula (H)

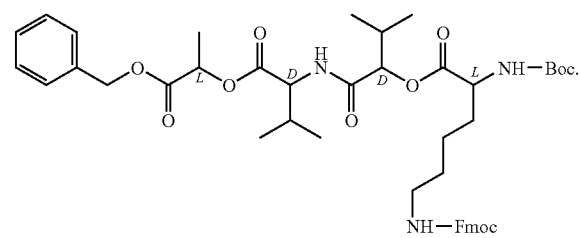

8. The process of claim 7 further comprising the step for coupling the compound of Formula (J)

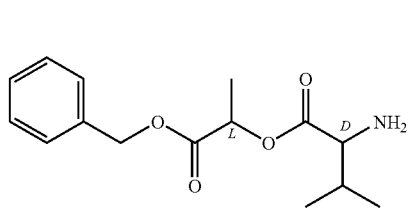

with the compound of Formula (K)

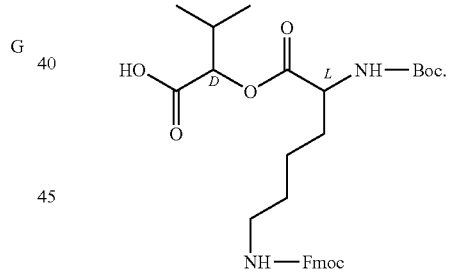

9. The process of claim 8 further comprising the step for removing the t-Butyloxycarbonyl group from the compound of Formula (L)

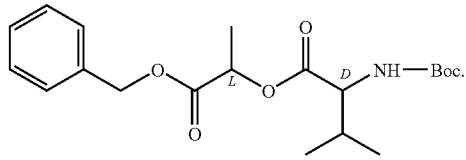

10. The process of claim 9 further comprising the step for converting the compound of Formula (M)

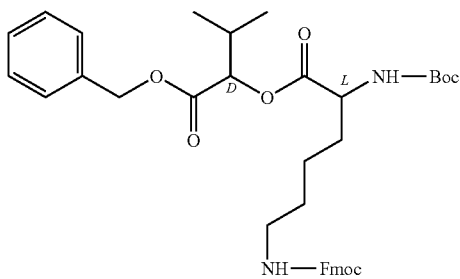

M into the compound of formula (K)

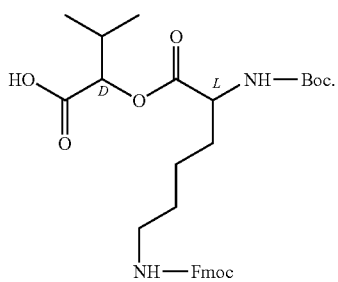

K

11. The process of claim 10 further comprising the step for coupling (R)-benzyl 2-hydroxy-3-methylbutanoate with the compound of Formula (N)

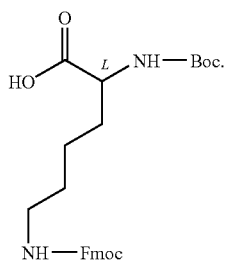

N

12. The process of claim 11 further comprising the step for coupling (R)-2-hydroxy-3-methylbutanoic acid with phenylmethanol.

13. The process of claim 12 further comprising the step for converting the compound of Formula (L)

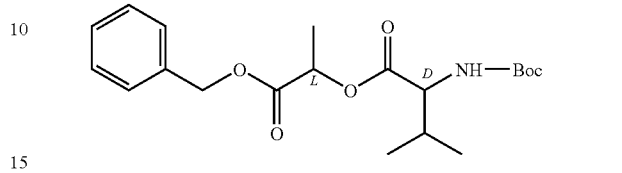

L into the compound of Formula (O)

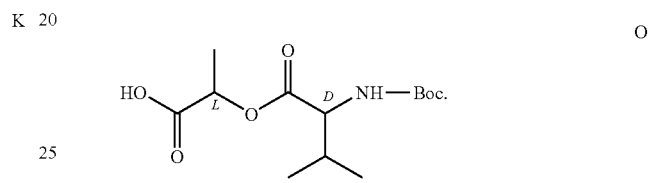

O

14. The process of claim 13 further comprising the step for coupling (S)-benzyl 2-hydroxypropanoate with (R)-2-(tert-butoxycarbonylamino)-3-methylbutanoic acid.

15. The process of claim 14 further comprising the step for coupling (S)-2-hydroxypropanoic acid with phenylmethanol.

16. A sensor comprising a self assembled monolayer of the compound of claim 1 on gold means for supporting said monolayer.

17. A method of making the sensor of claim 16 comprising:
- a step for selecting gold means of appropriate size for supporting the monolayer; and
- a step for immersing said gold means in a solution of the compound of claim 1,
- wherein a self assembled monolayer of said compound forms on said gold means.

\* \* \* \* \*